US008248597B2

(12) United States Patent
Goldberg

(10) Patent No.: US 8,248,597 B2
(45) Date of Patent: *Aug. 21, 2012

(54) METHOD, SYSTEM, AND COMPOSITIONS FOR CELL COUNTING AND ANALYSIS

(75) Inventor: Edward Michael Goldberg, Redwood City, CA (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 300 days.

This patent is subject to a terminal disclaimer.

(21) Appl. No.: 12/775,333

(22) Filed: May 6, 2010

(65) Prior Publication Data

US 2010/0261197 A1    Oct. 14, 2010

Related U.S. Application Data

(63) Continuation of application No. 12/009,659, filed on Jan. 22, 2008, now Pat. No. 7,738,094.

(60) Provisional application No. 60/897,618, filed on Jan. 26, 2007, provisional application No. 60/995,811, filed on Sep. 28, 2007.

(51) Int. Cl.
  *G01N 1/10* (2006.01)
(52) U.S. Cl. ...................................... 356/246
(58) Field of Classification Search ............ 356/39, 356/246
See application file for complete search history.

(56) References Cited

U.S. PATENT DOCUMENTS

| 5,528,045 A | 6/1996 | Hoffman et al. |
| 5,681,529 A * | 10/1997 | Taguchi et al. ............ 422/417 |
| 7,560,073 B1 | 7/2009 | Peter et al. |
| 7,781,226 B2 * | 8/2010 | McDevitt et al. ............ 436/518 |
| 2006/0252079 A1 | 11/2006 | Oldham et al. |
| 2007/0178009 A1* | 8/2007 | Sakaino et al. ............ 422/56 |

FOREIGN PATENT DOCUMENTS

| EP | 0737855 | 10/1996 |
| WO | WO 99/45384 | 9/1999 |

* cited by examiner

*Primary Examiner* — Roy M Punnoose
(74) *Attorney, Agent, or Firm* — Douglas A. Petry

(57) ABSTRACT

The present invention provides a low cost imaged-based system for detecting, measuring and/or counting labeled features of biological samples, particularly blood specimens. In one aspect, the invention includes a system for imaging multiple features of a specimen that includes one or more light sources capable of successively generating illumination beams each having a distinct wavelength band and a plurality of differentially excitable labels capable of labeling a specimen comprising multiple features, such that each different feature is labeled with a different differentially excitable label. System of the invention may further include a controller operationally associated with the one or more light sources for successively directing illumination beams onto the specimen so that each of the different differentially excitable labels is successively caused to emit an optical signal within the same wavelength band, an optical system capable of collecting such emitted optical signals and forming successive images corresponding to the labeled features of the specimen on a light-responsive surface to form successive sets of image data thereof, and a disposable cuvette for collection and optical analysis of non-red blood cells.

7 Claims, 11 Drawing Sheets

Counting Nucleated Cells
Propidium Iodide (impermeant) + SYTO-17
(permeant)

Counting cells in a CD3-APC/CD4-PECy5 image

CD3/CD4 Counting

CD3 & CD4 Cell Count Yield (versus Flow Cytometry) in Whole Blood

CBA protein assay for interleukin 2

METHOD, SYSTEM, AND COMPOSITIONS FOR CELL COUNTING AND ANALYSIS

This application claims priority from U.S. provisional applications 60/97,618 filed Jan. 26, 2007 and 60/995,811 filed Sep. 28, 2007, each of which is hereby incorporated by reference in its entirety.

BACKGROUND

Point-of-care testing and the search for effective biomarkers are important themes in biomedical research, e.g. Holland et al, Curr. Opin. Microbiol., 8: 504-509 (2005); Yager et al, Nature, 442: 412-418 (2006); Frank et al, Nature Reviews Drug Discovery, 2: 566-580 (2003); Sidransky, Nature Reviews Drug Discovery, 2: 210-218 (2002). Both endeavors are meant to improve the access and effectiveness of healthcare while reducing its costs. Point-of-care testing is analytical testing performed outside a central laboratory using a device that can be easily transported to the vicinity of the patient and that can be operated under field conditions without highly specialized personnel. In many acute care medical and bio-defense monitoring applications, rapid sample processing and test readouts are also required, e.g. Raja et al, Clinical Chemistry, 48: 1329-1337 (2002).

A biomarker is a characteristic that is objectively measured and evaluated as an indicator of normal biological processes, pathogenic processes, or pharmacological responses to a therapeutic intervention, Atkinson et al, Clin. Pharmacol. Ther., 69: 89-95 (2001). Biomarkers vary widely in nature, ease of measurement, and correlation with physiological states of interest, e.g. Frank et al (cited above). Most point-of-care devices are designed to measure molecular biomarkers that have been extracted from a sample or specimen or that are found directly in a biological fluid, such as blood, Holland et al (cited above). There is significant interest in measuring cellular markers in point-of-care devices, but cellular markers typically require some form of imaging or a fluidics system in order to make cell-specific measurements, thereby adding a significant technical challenge over that posed by the measurement of molecular markers, e.g. Shapiro, Cytometry A, 60A: 115-124 (2004); Shapiro et al, Cytometry A, 69A: 620-630 (2006); Rodriquez et al, PLOS Medicine, 2(7): e182 (2005); Janossy et al, Clinical Cytometry, 50: 78-85 (2002); Toner et al, Annu. Rev. Biomed. Eng., 7: 77-103 (2005); and the like.

Point-of-care tests could be carried out on a wide range of sample types, including not only samples from individual organisms, such as medical, veterinary, or plant samples, but also samples from various environments, such as soils, water systems, air conditioner systems, surfaces in public places, such as transportation systems, and the like. Among medical samples, biological fluids, such as blood, saliva, tear duct fluid, urine, and the like, are especially amenable for use with point-of-care assays, as they are usually much more accessible than solid tissues. Among such biological fluids from which cellular or molecular markers can be obtained, blood is the sample of choice, whenever biologically relevant, because it systemic, it is easily accessible, and it contains a rich and dynamic suspension of cells and molecules whose composition reflects states of health and disease. In particular, there is great interest in being able to count certain subsets of non-red blood cells that are correlated with disease susceptibilities, disease progression, drug responsiveness, and the like, e.g. Guisset et al, Intensive Care Med., Epub (Nov. 8, 2006); Shaked et al, Curr. Cancer Drug Targets, 5: 551-559 (2005); Madjid et al, J. Am. Coll. Cardiol., 44: 1945-1956 (2004); Janossy et al (cited above); Rodriquez et al (cited above). Unfortunately, currently available analyzers for such markers suffer from one or more drawbacks that limit their widespread use, including complex preparation steps involving separation and/or cell lysis, involvement of specialized personnel, lack of portability, high cost, lack of sensitivity, and the like.

In view of the above, several medical and biotechnology fields would be significantly advanced with the availability of techniques, capable of point-of-care operation, which permitted facile and flexible measurements of cellular markers, particularly in biological fluids, such as blood.

SUMMARY OF THE INVENTION

The present invention provides a low cost imaged-based system for detecting, measuring and/or counting labeled features of biological samples, particularly blood specimens.

In one aspect, the invention includes a system for imaging multiple features of a specimen comprising the following elements: (a) one or more light sources capable of successively generating illumination beams each having a distinct wavelength band; (b) a plurality of differentially excitable labels capable of labeling a specimen comprising multiple features, such that each different feature is labeled with a different differentially excitable label; (c) a controller operationally associated with the one or more light sources for successively directing illumination beams onto the specimen so that each of the different differentially excitable labels is successively caused to emit an optical signal within the same wavelength band; and (d) an optical system capable of collecting such emitted optical signals and forming successive images corresponding to the labeled features of the specimen on a light-responsive surface to form successive sets of image data thereof.

In another aspect, the invention includes an apparatus for analyzing in a blood specimen non-red cells labeled with a plurality differentially excitable labels, such apparatus comprising: (a) a sample chamber capable of containing a blood specimen and having a dimension along a light collection axis that precludes the formation of a light-obstructing layer of red blood cells; (b) multiple light sources each capable of illuminating the blood specimen with an illumination beam having a distinct wavelength band; (c) a controller coupled to the multiple light sources for successively directing the illumination beam of each light source onto the specimen so that each of the plurality of differentially excitable labels is successively caused to emit an optical signal within the same wavelength band; (d) an optical system capable of collecting such emitted optical signals and forming successive images corresponding thereto on a light-responsive surface to form successive sets of image data, wherein the non-red cells in the blood specimen are enumerated by analyzing the successive sets of such image data.

In another aspect, the invention includes a probe composition for use in labeling one or more of a plurality of different cellular analytes in a sample, comprising a mixture of analyte-specific probes, each capable of binding specifically to a different analyte, wherein each probe is characterized by (a) a binding compound specific for a cellular analyte under binding conditions, and (b) attached to the binding compound an optical label, the optical label of each different probe having a different excitation band and the optical labels of all probes emitting optical signals within the same wavelength range. Preferably, such same wavelength range is separate from the excitation bands of the optical labels of the probe composition.

In another aspect, the invention includes a disposable blood collection cuvette for optical analysis of non-red blood cells, the cuvette that comprises (a) a mixing chamber having an inlet for accepting a sample of whole blood, the mixing chamber further comprising a dried reagent capable of dissolving on contact with the whole blood sample and containing a probe composition that comprises a plurality of analyte-specific probes, each capable of binding specifically to a different cellular analyte of a non-red blood cell, wherein each probe is characterized by (i) a binding compound specific for a cellular analyte under binding conditions, and (ii) attached to the binding compound an optical label, wherein the optical label of each different probe has a different excitation band and the optical labels of all probes emit optical signals within the same wavelength range; and (b) a sample chamber fluidly connected to the mixing chamber so that a sample in the mixing chamber is transferred to the sample chamber by capillary action, the sample chamber having an optically transmissive wall and a dimension perpendicular thereto substantially equivalent to the diameter of a non-red blood cell so that optical signals generated by probes attached to cellular analytes thereof are not obstructed by red blood cells of the sample. Preferably, said dimension is selected so that it substantially precludes the formation of a light-obstructing layer of enucleate red blood cells between a cell of interest and said optically transmissive wall.

In still another aspect, the invention includes a disposable blood collection cuvette for optical analysis of non-red blood cells, wherein the cuvette comprises (a) a sample chamber capable of receiving a sample of whole blood, the sample chamber being disposed in a body and having at least one optically transmissive wall and a dimension perpendicular thereto substantially equivalent to the diameter of a non-red blood cell so that optical signals generated by probes attached to cellular analytes thereof are not obstructed by red blood cells of the sample; and (b) a dried reagent in the sample chamber that upon combination with the sample dissolves to form a probe composition that comprises a plurality of analyte-specific probes, each capable of binding specifically to a different cellular analyte of a non-red blood cell, wherein each probe is characterized by (i) a binding compound specific for a cellular analyte under binding conditions, and (ii) attached to the binding compound an optical label, wherein the optical label of each different probe has a different excitation band and the optical labels of all probes emit optical signals within the same wavelength range.

In another aspect, the invention includes an apparatus for imaging specimens labeled with a plurality of fluorescent labels, the apparatus comprising the following elements: (a) one or more light emitting diodes capable of illuminating the specimen, each light emitting diode generating an illumination beam with a distinct wavelength band; (b) a controller coupled to the light emitting diodes for directing illumination beams thereof onto the specimen so that each of the plurality of fluorescent labels is caused to emit in sequence an optical signal; and (c) an optical system capable of collecting the emitted optical signals and forming an image corresponding thereto on a light-responsive surface to produce image data, wherein the optical system includes a color camera capable of capturing multiple optical signals having different wavelengths. Preferably, said one or more light emitting diodes is a plurality of light emitting diodes, and said optical system produces a plurality of sets of image data, each such set corresponding to optical signals generated in response to illumination by a different one of said light emitting diodes.

The invention overcomes many cost and efficiency drawbacks of prior art approaches to point-of-care systems for rapid analysis of medical and environmental samples, including blood, saliva, urine, and the like. Particular embodiments of the invention are well suited for low cost and efficient detection and counting of a variety of cellular components and/or pathogens that may be present in whole blood, including, but not limited to, non-red blood cells, lymphocytes, such as CD3+ cells, CD4+ cells, CD8+ cells, blood parasites, such as malaria, and the like.

DETAILED DESCRIPTION OF THE INVENTION

Figure 1:
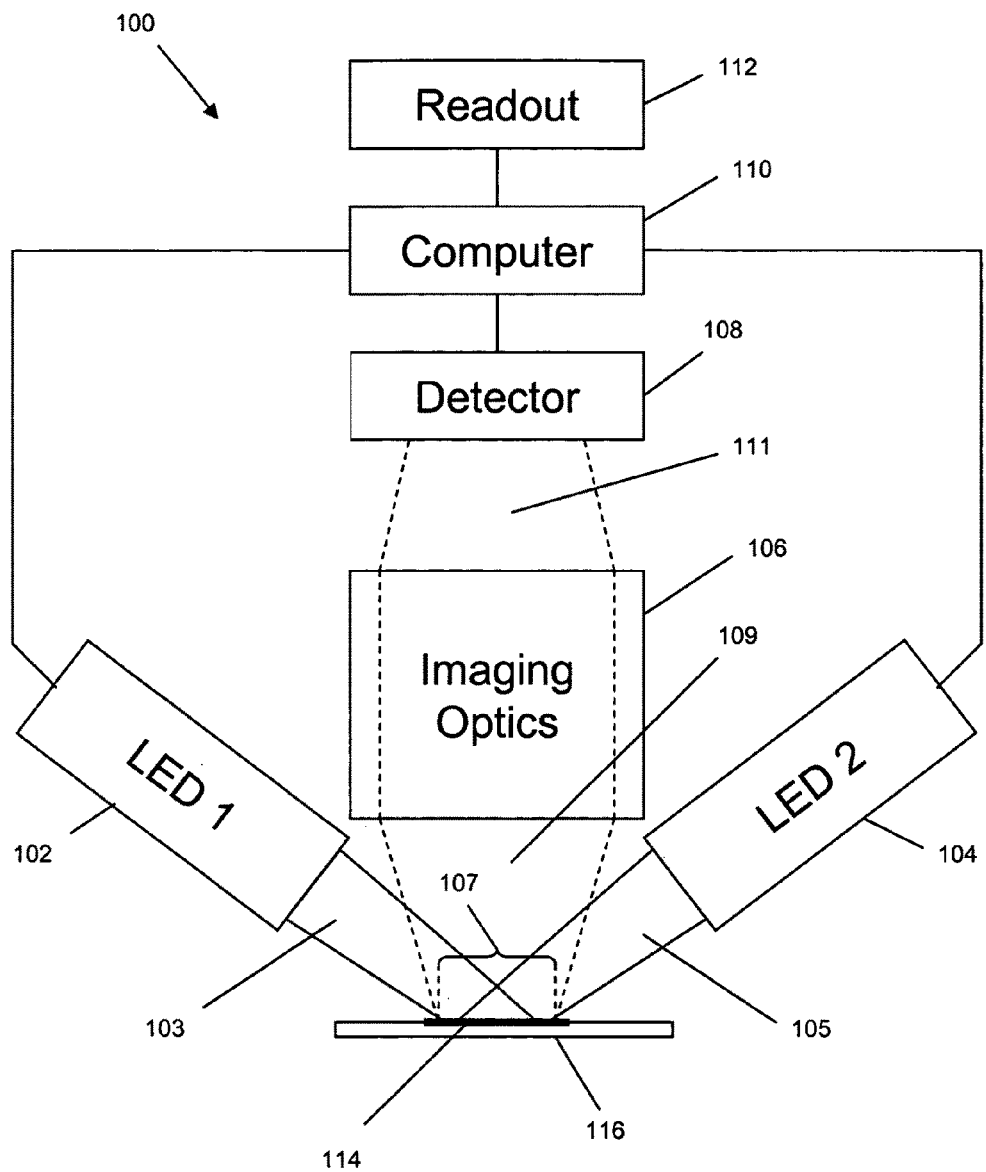
FIG. 1 illustrates diagrammatically an optical system for use with the invention.

The practice of the present invention may employ, unless otherwise indicated, conventional techniques from molecular biology (including recombinant techniques), cell biology, immunoassay technology, microscopy, image analysis, and analytical chemistry, which are within the skill of the art. Such conventional techniques include, but are not limited to, detection of fluorescent signals, image analysis, selection of illumination sources and optical signal detection components, labeling of biological cells, and the like. Such conventional techniques and descriptions can be found in standard laboratory manuals such as *Genome Analysis: A Laboratory Manual Series* (Vols. I-IV), *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press);

Murphy, Fundamentals of Light Microscopy and Electronic Imaging (Wiley-Liss, 2001); Shapiro, Practical Flow Cytometry, Fourth Edition (Wiley-Liss, 2003); Herman et al, Fluorescence Microscopy, $2^{nd}$ Edition (Springer, 1998); all of which are herein incorporated in their entirety by reference for all purposes.

The invention provides systems, methods, and compositions for measuring and counting cells, micelles, particles, and/or analytes in a sample by sequentially illuminating the sample with illumination beams having different wavelength ranges that correspond to the excitation bands of labels directly or indirectly bound or attached to the analytes, cells, or particles in the sample. After each illumination in such a sequence, optical signals are collected to form an image, so that a set of images are formed each containing image data that is analyzed to provide counts and/or measurements of the population of cells, particles, and/or analytes. In one aspect, a plurality of illumination beams is employed that have substantially non-overlapping wavelength ranges. Such plurality of illumination beams may be in the range of from 2 to 6, or in the range of from 2 to 4, or in the range of from 2 to 3. A plurality of illumination beams may be generated by a variety of methods and apparatus available to those of ordinary skill, including by lasers, filament and arc lamps, and the like. In one embodiment, illumination beams are generated using light emitting diodes (LEDs), or like solid state devices. Exemplary LED light sources include Luxeon™ LEDs that have wavelength peaks in green (530 nm), cyan (505 nm), blue (470 nm), and royal blue (455 nm), commercially available from Lumileds Lighting LLC (San Jose, Calif.). Guidance in selecting particular LEDs for use with the invention is widely available in the technical literature, such as Luxeon Star Technical Data Sheet DS23 (Philips Lumileds Lighting Company, San Jose, 2006); Luxeon Star V Technical Data Sheet DS30 (Lumileds Lighting, U.S., LLC, San Jose, Calif., Sep. 20, 2004); and the like. Usually, light sources are used with conventional filters and other optical components for generating illumination beams of desired wavelength ranges and intensity distributions.

I. Optical Systems

A wide variety of optical systems can be employed with the invention. Generally, such systems provide one or more illumination beams for sequentially illuminating a sample in distinct wavelength ranges, an image collection device for recording image data from the illuminated sample, and a controller that controls the operation of the illumination beams and image collection device so that image data sets are sequentially collected.

In one aspect, the invention includes a system comprising an image collection device used in concert with sets of differentially excitable dyes attached to probes specific for cell, particles, or analytes of interest in a sample. In other words, such a system comprises an apparatus of the following components for imaging samples or specimens labeled with a plurality differentially excitable labels: (a) multiple light sources each capable of illuminating the specimen with an illumination beam having a distinct wavelength band; (b) a controller coupled to the multiple light sources for successively directing the illumination beam of each light source onto the specimen so that each of the plurality of differentially excitable labels is successively caused to emit an optical signal within the same wavelength band; and (c) an optical system capable of collecting such emitted optical signals and forming successive images corresponding thereto on a light-responsive surface to form successive sets of image data. One embodiment of the above apparatus is illustrated in FIG. 1. System (100) comprises several components, including a plurality of light sources, shown as LED 1 (102) and LED 2 (104), for sequentially illuminating observation area (107) of sample (114) disposed on or in sample platform (116), imaging optics (106) for collecting optical signals (109) generated from probes in and/or on the sample in response to illumination beams (103) and (105) and for directing (111) the collected signals to detector (108), which comprises a light-responsive surface, such as a CCD or CMOS element, on which optical signals (109) form an image and from which successive sets of image data are recorded. Preferably, operation of system (100) is under the control of computer (110) that (a) controls the timing and duration of illumination beams (103) and (105), (b) controls detector (108) for collecting and transferring image data to one or more databases, (c) analyzes image data to produce a readout for readout component (112), and like operations. Sample platform (116) may vary widely in design and functional capabilities, but generally requires that a sample be disposed in a substantially planar geometry that is consistent with collecting a plurality of optical signals in parallel and forming an image on a detector. Preferably, a sample disposed on sample platform (116) is static and not flowing or moving; or if motion is present, it is sufficiently slow that successive images may be collected that are capable of alignment during image analysis. Sample platform (116) may comprise conventional microscope slides, sample chambers or cuvettes used in microscopy, culture plates, microfluidic devices, or the like. In one aspect, described more fully below, sample platform (116) comprises a disposable cuvette that is designed for detection of non-red cell components in whole blood. In another aspect, sample platform (116) comprises a cuvette having a sample chamber with a geometry that permits a known volume to be surveyed whenever such cuvette is used with system (100). In one embodiment, such a sample chamber has a substantially planar geometry wherein (a) a floor (or bottom wall) and a ceiling (or top wall) are parallel to one another and (preferably) perpendicular to the minimal light path to imaging optics (106) and (b) the perpendicular distance between the top and bottom walls is substantially equivalent to the diameter of the cells or particles being detected. Whenever such sample chamber is disposed in observation area (107), which is known or determinable, the cells or particles will be in a known (or determinable) volume, thereby permitting concentrations of the particles or cells to be measured. "Substantially equivalent" in reference to the perpendicular distance, or dimension, between the top and bottom walls of a sample chamber means that, in a whole blood sample, optical signals from non-red cells or particles in observation area (107) are detectable. In other words, a layer of red blood cells (or other debris) that may be between a labeled cell or particle and the top wall of the chamber does not completely obstruct transmission of optical signals. In one aspect, where white blood cells are labeled and detected, such as CD4+ cells, the perpendicular distance between a top wall and a bottom wall is in the range of from 40 to 120 μm, or in the range of from 50 to 100 μm. The nature of readout component (112) may vary widely from a simple numerical display to an information-rich graphic user interface. In one embodiment, a simple numerical readout is provided by readout component (112) that gives counts of one or more predetermined cell or particle types. In another embodiment, readouts comprise concentrations of or one or more predetermined cell or particle types. And in still another embodiment, readouts comprise simple "yes or no" indicators as to whether threshold levels (e.g. counts or concentrations) of cells, particles, or other analytes have or have not been passed.

Figure 2:
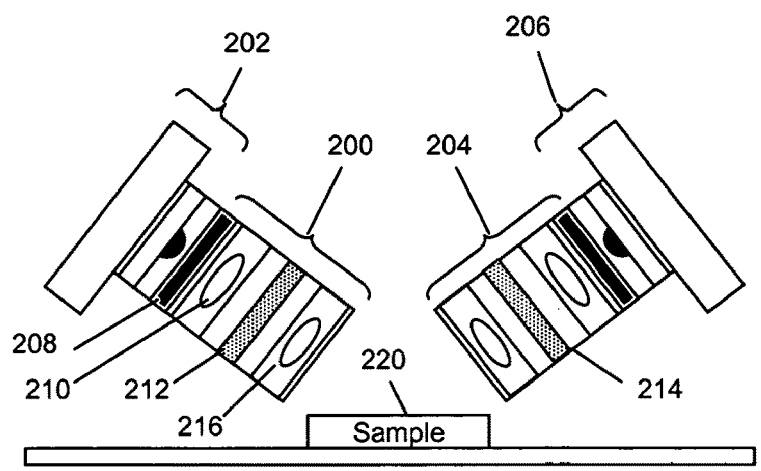
FIG. 2 illustrates diagrammatically a system of optical components for use with LEDs to condition excitation beams.

In embodiments employing LEDs to generate illumination beams, the emissions from the selected LED may be conditioned using optical components, as illustrated in FIG. 2 for a two-LED system. First LED (202) and second LED (206) have conditioning optics (200) and (204), respectively, that each comprise diffuser (208), lens (210), bandpass filter (212), and lens (216). A purpose of conditioning optics (200) and (204) is to provide spatially uniform illumination of sample (220).

Figure 10:
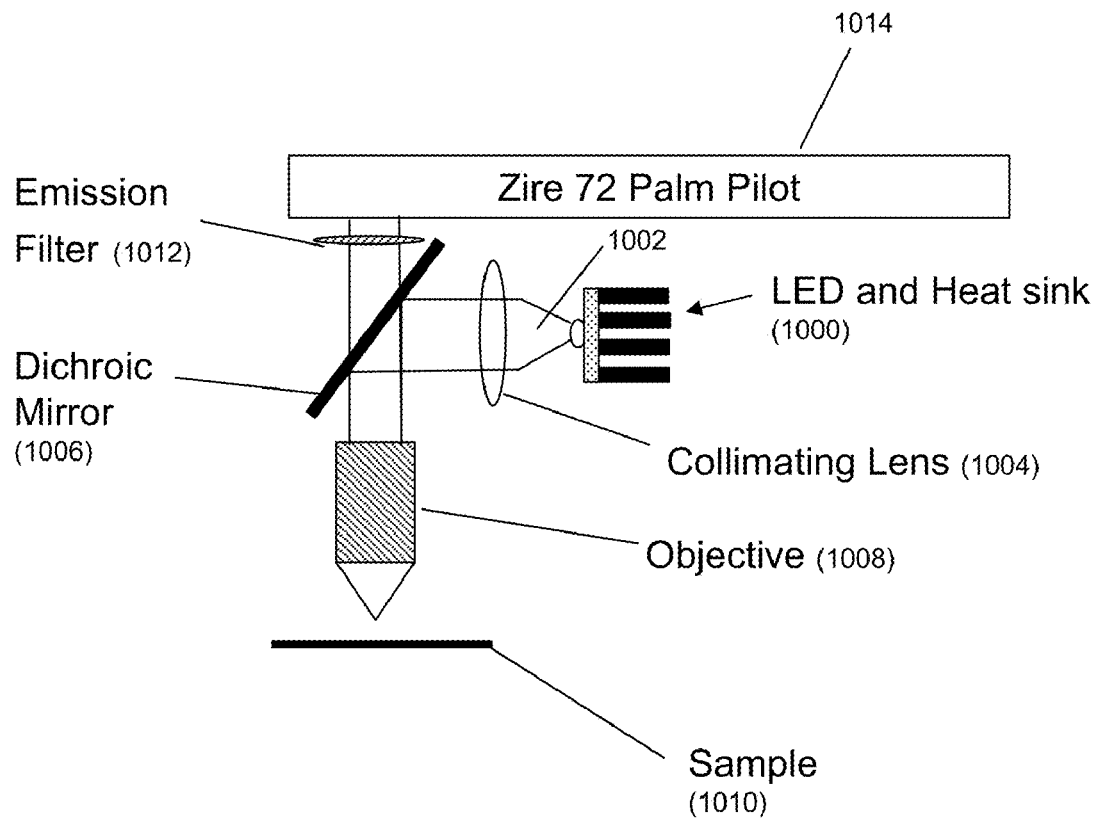
FIG. 10 diagrammatically illustrates an optical system for use with the invention.

FIG. 10 illustrates an epi-illumination optical system for use with the invention. LED (1000) generates illumination beam (1002) that is collimated by lens (1004) and directed to dichroic mirror (1006) and then to objective (1008). Light from illumination beam (1002) is focused onto sample (1010) where fluorescent labels are excited to emit fluorescent signals. Fluorescent signals collected by objective (1008) are directed through dichroic mirror (1006), optionally through emission filter (1012), then onto a light-responsive surface, in this illustration, a camera of a commercially available personal digital assistant, Zire 72 Palm Pilot, which also contains a display for observing a sample. Additional illumination beams may be added by adding additional dichotic mirrors along the optical path between objective (1008) and emission filter (1012).

II. Differentially Excitable Probes

In another aspect, the invention provides compositions of differentially excitable probes for use in labeling one or more of a plurality of different analytes in a sample. Generally, probe compositions of the invention comprise a mixture of analyte-specific probes, each capable of binding specifically to a different analyte, wherein each probe is characterized by (a) a binding compound specific for an analyte, such as a cellular analyte, under binding conditions, and (b) attached to the binding compound an optical label, wherein the optical label of each different probe has a different excitation band and the optical labels of all probes emits optical signals within the same wavelength range. Usually, the latter wavelength range does not overlap with any of the excitation bands. Preferably, optical labels are fluorescent labels, such as fluorescent dyes, capable of generating fluorescent signals. However, other optical labels may be used with the invention, such as plasmon resonance particle when used under dark field illumination conditions. In one aspect, probe compositions of the invention include at least one probe specific for each of a plurality of different analytes. In another aspect, such plurality is in the range of from 2 to 8; or in another aspect, in the range of from 2 to 4; or in another aspect, in the range of from 2 to 3; and in another aspect, such plurality is at least 3; or is in the range of from 3 to 4. An important feature of a probe composition of the invention is that analytes in a sample labeled with different probes of the composition may be detected sequentially by the successive excitation of the optical labels of each probe using the illumination beam specific for such optical label. Usually, such successive excitation is temporally non-overlapping in that when each illumination beam is directed to the sample in a separate time interval. In other words, the illumination beams are successively directed to a sample one at a time. Preferably, in operation, optical signals from each excitation are imaged on a light-responsive surface of a detector from which image data is generated and stored for analysis. When optical signals of the probes are restricted to a narrow wavelength range, image degradation due to chromatic aberrations of lens in the optical path is reduced or eliminated.

Figure 3:
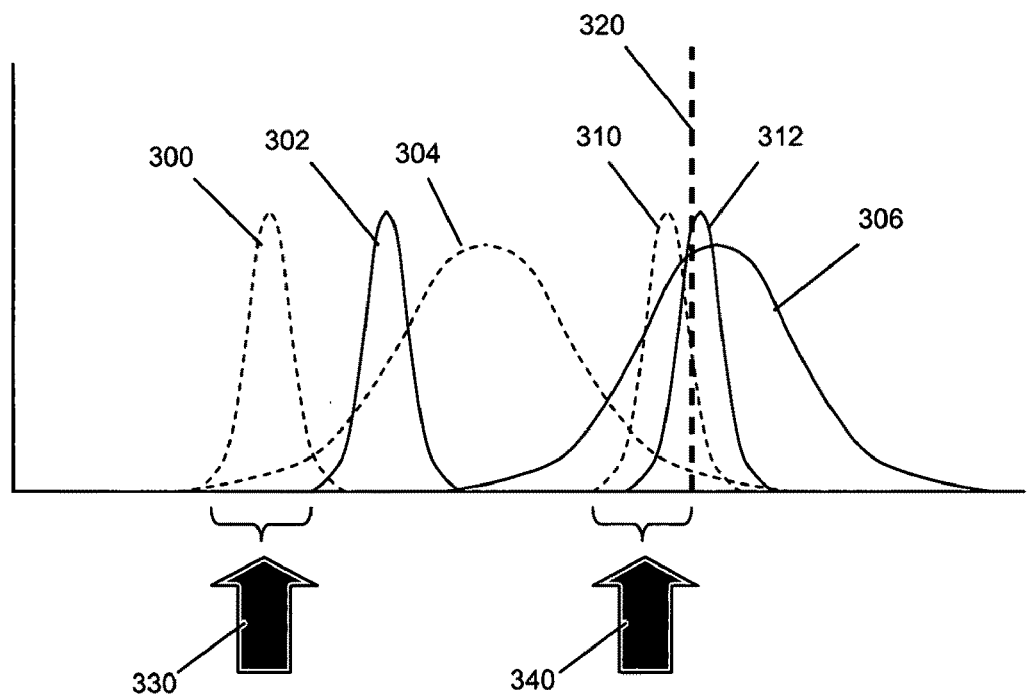
FIG. 3 illustrates the principle for selecting optical labels for probe compositions of the invention.

The principle of operation of one embodiment of probe compositions of the invention are illustrated in FIG. 3, which shows the excitation and emission spectra of optical labels of a composition of the invention that consists of two probes. A first probe has an optical label that employs fluorescence resonance energy transfer (FRET), wherein a donor molecule has absorption, or excitation, spectrum (300) (dashed curve) and emission spectrum (302) (solid curve) and an acceptor molecule has absorption spectrum (304) (dashed curve), which overlaps (302), and emission spectrum (306) (solid curve). A second probe has as an optical label a fluorescent molecule with absorption spectrum (310) (dashed curve) and emission spectrum (312) (solid curve). Dashed line (320) indicated the highest wavelength boundary of the range over which optical signals are collected. Thus, whenever a sample labeled with the first and second probes are illuminated with a first illumination beam (330) having wavelength range as indicated a first optical signal is collected consisting of acceptor molecule emissions (306), and whenever such sample is illuminated with a second illumination beam (340) having wavelength range as indicated a second optical signal is collected within the same wavelength range, but consisting of emissions (312). An exemplary donor-acceptor pair for the first probe is cyanine 3-allophycocyanin (Cy3-APC), and an exemplary optical label of the second probe is cyanine 5 (Cy5). Exemplary optical labels for a three-probe composition includes cyanine 7 (Cy7) (as donor and acceptor for a first probe), APC-Cy7 (APC as donor and Cy7 as acceptor for a second probe), and PE-Cy7 (PE as a donor and Cy7 as acceptor for a third probe).

Figure 4A:
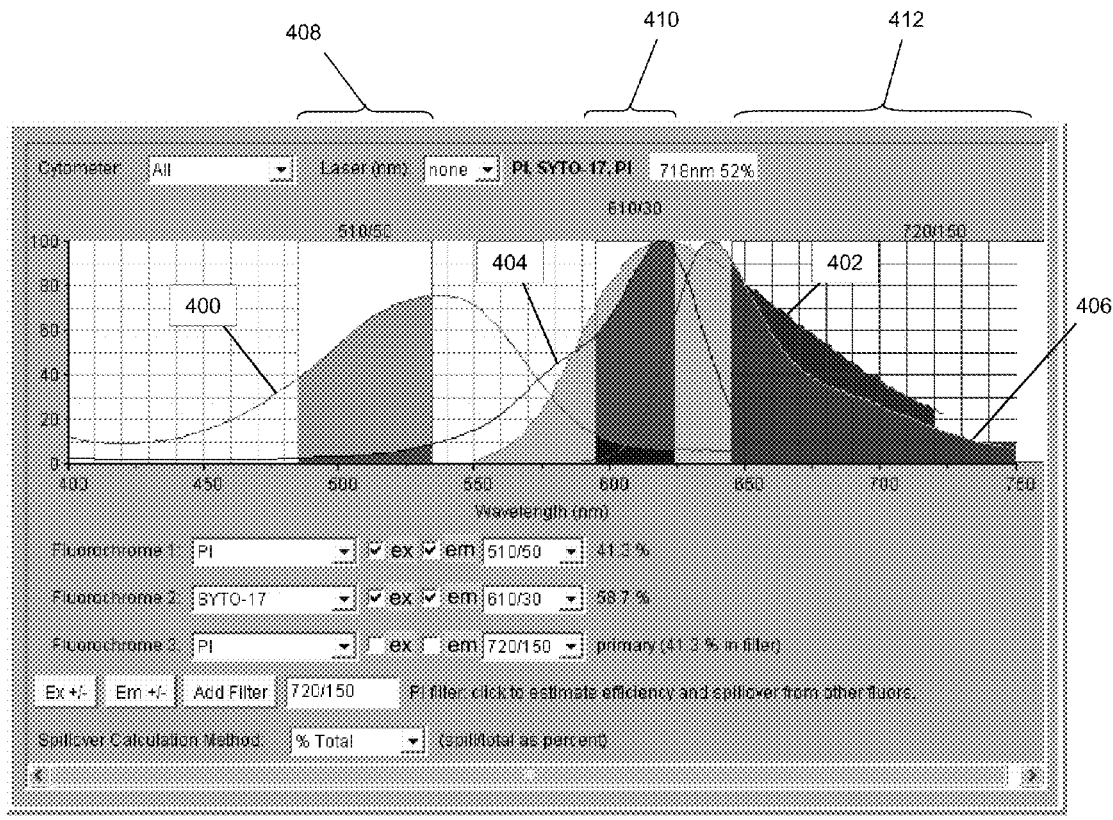
FIG. 4A shows absorption curves for two fluorescent labels used in the example that have distinct excitation bands but that are capable of emitting substantial fluorescence within the same wavelength range.
Figure 4B:
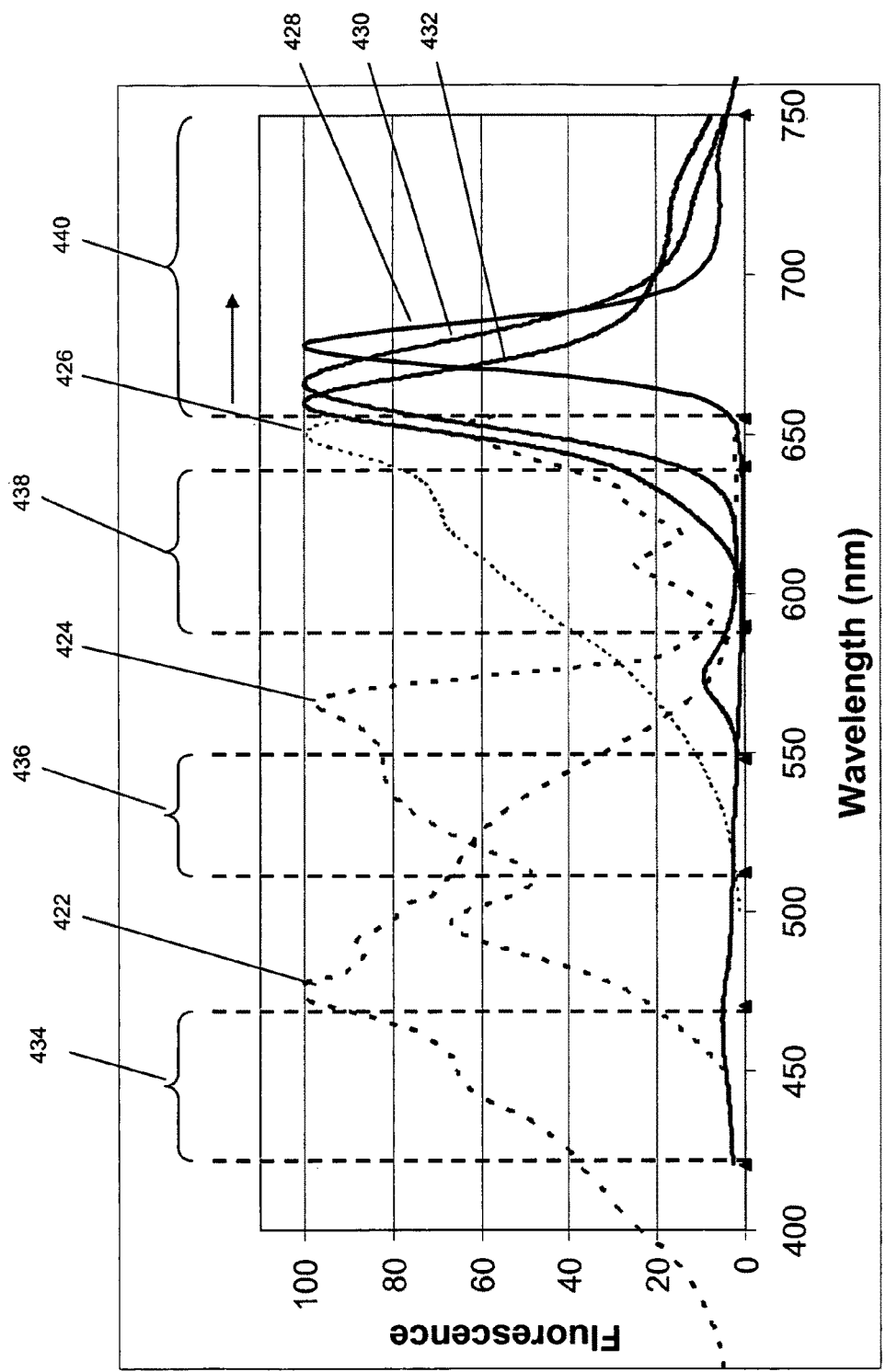
FIG. 4B shows absorption and emission curves of three fluorescent labels that may be sequentially excited by three different excitation beams and that emit fluorescence signals in the wavelength range above 650 nm.

Further exemplary probe compositions for two-label and three-label probes are illustrated in FIGS. 4A (described below) and 4B, respectively. FIG. 4B illustrates excitation and emission wavelength profiles for three fluorescent dyes and wavelength bands of associated illumination beams of a probe composition of the invention. The dyes are peridinin chlorophyll protein (PerCP) having excitation profile (422) and emission profile (428), phycoerythrin-Cy5 (PECy5) conjugate having excitation profile (424) and emission profile (430), and allophycocyanin (APC) having excitation profile (426) and emission profile (432). Such dyes may be sequentially excited by applying illumination beams having wavelengths in the ranges of about 420-470 nm for PerCP (434), about 515-550 nm for PECy5 (436), and about 590-640 nm for APC (438). Such illumination beams may be generated by LEDs, for example, Luxeon Star Royal Blue, Green, and Red-Orange LEDs, respectively. The fluorescent signals generated by the probes are conveniently separated from scattered light using bandpass filter (440) that transmits light only above about 650 nm. The above dyes are readily conjugated to binding compounds, such as antibodies, using conventional techniques, e.g. Hemanson, Bioconjugate Techniques (Academic Press, New York, 1996).

In another aspect, probe compositions comprise binding compounds are labeled with plasmon resonance particles (PRPs). Such probe compositions are particularly useful when employed with a dark-field illumination system so that only scattered light from the PRPs is collected. PRPs suitable for use with probe compositions of the invention are disclosed in the following references that are incorporated by reference: Schultz et al, Proc. Natl. Acad. Sci., 97: 996-1001 (2000); Schultz et al, U.S. Pat. No. 6,180,415; Prober et al, U.S. Pat. No. 7,122,384; and the like. In this embodiment, PRPs are selected so that each scatters maximally the light from a distinct illumination beam.

III. Cuvette for Whole Blood Measurements.

In an aspect of the invention, a disposable cuvette is provided for use with the system of the invention for making measurements on whole blood. In one embodiment, such a cuvette is used to count predetermined blood cell types, e.g.

non-red cells, in a determinable volume; thus, either cell counts or concentrations of such predetermined cell types can be given as a readout. Generally, a disposable cuvette of the invention comprises (a) a sample chamber capable of receiving a sample of whole blood, the sample chamber being disposed in a body and having at least one optically transmissive wall and a dimension perpendicular thereto substantially equivalent to the diameter of a non-red blood cell to be analyzed so that optical signals generated by probes attached to cellular analytes thereof are not obstructed by red blood cells of the sample; and (b) a dried reagent in the sample chamber that upon combination with the sample dissolves to form a probe composition that comprises a plurality of analyte-specific probes, each capable of binding specifically to a different cellular analyte of a non-red blood cell, wherein each probe is characterized by (i) a binding compound specific for a cellular analyte under binding conditions, and (ii) attached to the binding compound an optical label, wherein the optical label of each different probe has a different excitation band and the optical labels of all probes emit optical signals within the same wavelength range. Preferably, such a disposable cuvette is used with an optical system as described above, which includes a platform for receiving the cuvette so that it has a fixed position with respect to the illumination beams and imaging optics. Such fixed position will align the imaging optics so that optical signals can be collected from the sample chamber of the cuvette. The design and fabrication of disposable sample holders for observing or measuring properties of biological fluids, such as blood parameters, are disclosed in the following references that are incorporated by reference: U.S. Pat. Nos. 6,723,290; 6,869,570; 5,674,457; 5,200,152; 6,638,769; 4,088,448; and the like.

One embodiment of a cuvette of the invention is illustrated diagrammatically in FIGS. 5A-5D. In one form, cuvette (500) comprises body (501), that may be glass, plastic, or like materials, or combinations thereof; and at least one sample chamber (502) that is connected to inlet port (504) by passage (506). In one aspect, for use in whole blood measurements, sample chamber (502) may hold a volume of sample fluid in the range of from 5 to 100 µL, or from 5 to 50 µL. Cuvette (500) may also include an exhaust port (not shown) connect to sample chamber (502) to allow sample to enter the chamber without the formation of back pressure. Alternative approaches for loading sample into sample chamber (502) may also be employed, such as capillary action, suction, centrifugal force, and the like. An important feature of cuvette (500) is the collection of optical signals from a defined or determinable volume (512) so that concentration determinations can be made from image data, e.g. of selected cell types. Volume (512) is defined by the distance (e.g. 528 in FIG. 5C) between top wall (514) and bottom wall (516) of cuvette (500) and the area, or field of view, of the imaging optics, indicated by cone (508) and direction (510) at which optical signals are collected. An important feature of the optical system of the invention in this embodiment is that the depth of field of the objective be greater than or equal to the distance (528 or 518) between top wall (514) and bottom wall (516), so that optical signals from all the objects in volume (512) are collected. Preferably, top wall (514) is suitable for passing optical signals for collection and is substantially parallel with bottom wall (516). In other embodiments, cuvettes of the invention may include addition chambers, for example, for holding reagents and/or for mixing sample with such reagent prior to viewing. In one aspect, cuvettes of the invention further contain dried reagents, e.g. including probe compositions, salts, buffers, lysing agents if necessary, and the like, either directly disposed in sample chamber (502), or in other embodiments, contained in a separate mixing chamber (505) for activation and mixing with a sample prior to transfer to sample chamber (502).

Figure 5A:
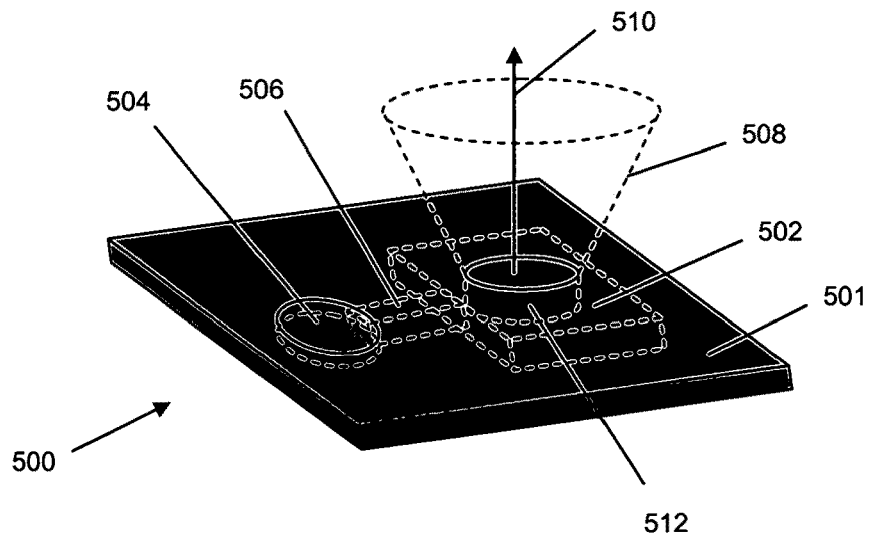
FIGS. 5A-5D illustrate diagrammatically an embodiment of a sample cuvette for use with the invention for detecting and analyzing non-red blood cells and/or other cells or microorganisms in whole blood.
Figure 5B:
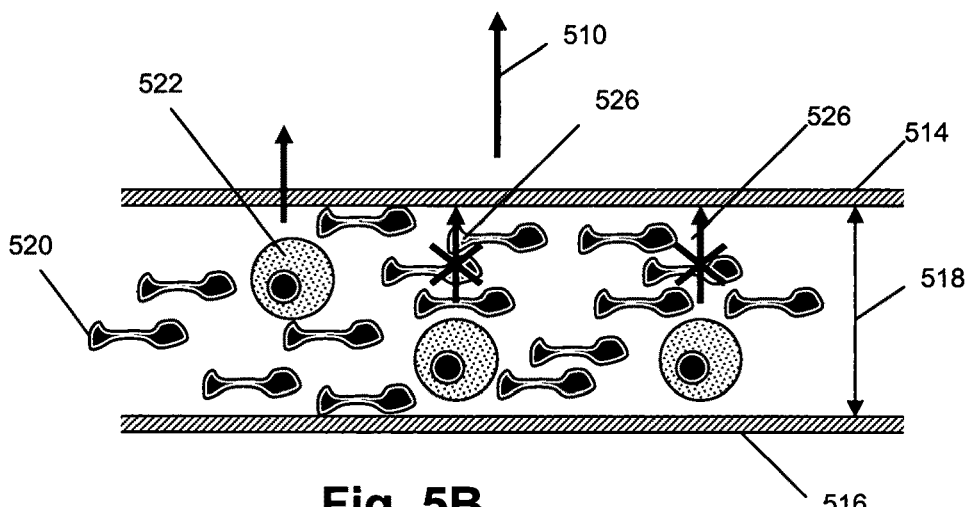
Figure 5C:
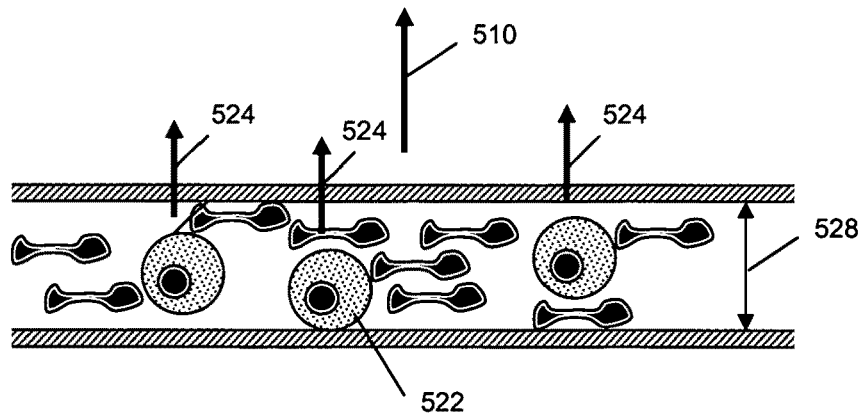
Figure 5D:
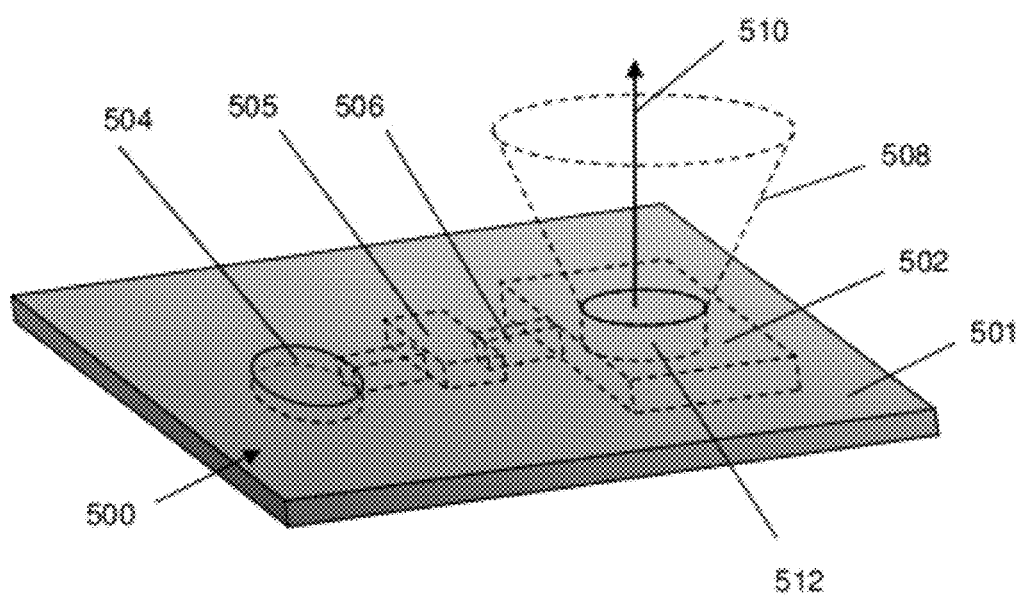

As mentioned above, the distance between the top wall (514) and bottom wall (516) of sample chamber (502) is important for analysis of whole blood samples. If the distance is too great, e.g. (518) of FIG. 5B, then enucleate red blood cells (520) may obstruct (526) the passage optical signals generated from cell types of interest (522), in which case such cells may not be counted, leading to an under estimate of cell numbers or concentration. In accordance with the invention, and as illustrated in FIG. 5C, distance (518) between top wall (514) and bottom wall (516) of sample chamber (502) is substantially equivalent to the diameter, or effective diameter, of cell types of interest (522), so that obstructing layers of enucleate red blood cells cannot form between a cell of interest (522) and top wall (514), and optical signals therefrom (524) all from sample chamber (502) to the imaging optics. In one aspect, sample chamber (502) has a distance (518) substantially equivalent to the depth of field of the imaging optics. In another aspect, sample chamber (502) has a distance (518) in the range of from 10 to 100 µm, or from 10 to 50 µm, or from 20 to 50 µm.

EXAMPLE

In this example, an imaging system for use with the invention was constructed and tested by counting cells or particles in various samples. The system had a design that followed that illustrated in FIG. 1. Two different grey scale cameras were employed as detectors. The first was a Sensovation Samba EZ140 TC-cooled (20° C. below ambient) camera with 1392×1024 pixels with square 6.45 um pixel. The second camera was a Point Grey Research Dragonfly2 industrial vision camera with 1024×768 square (4.65 um) pixels. Either of two imaging lens designs was used. One design was a pair of doublet spherical lenses with the excitation filter positioned between them. This system possessed a relatively high N.A. (~0.33) and worked well for fields of view up to about 2 mm. Beyond this distance, astigmatic distortion is noticeable and increases rapidly as image field increased. To address this condition, a second lens setup was employed. This was a commercial camera lens (Nikon 18-55 mm f/3.5-5.6G ED AF-S DX Zoom) with one hybrid aspherical element and one extra-low dispersion element. This lens has excellent low distortion, better depth-of-field, and enabled imaging over a 4 mm field of view with no detectable astigmatism, although it has a lower N.A. of ~0.1. This decrease in light collection efficiency was not enough to cause any detectable decline in accuracy for cell enumeration. The design with the DragonFly2 camera and Nikon DX zoom lens is the preferred configuration for cost and image quality.

LED light sources, or illuminators, were each fitted with their own excitation filter within the lamp housings. In the case of propidium iodide (PI) or phycoerythrin/phycoerythrin (PE/PE) tandem illumination, the lamp is a Luxeon V Star Cyan LED with a Lambertian radiation pattern, nominal peak wavelength of 505 nm (spectral half width of ±30 nm), and a nominal flux of 570 mW at 700 mA current. The excitation filter is a HQ510/50 filter from Chroma. For SYTO 17 or APC excitation, the lamp is a Luxeon III Star Red-Orange LED (Lambertian radiation pattern) with a nominal peak wavelength of 617 nm (spectral half-width of ±18 nm) and nominal flux of 600 mW at 1400 mA current. A Chroma HQ610/30 emission filter was used for the Red-Orange light. LEDs were used at lower than maximum rated currents. Specifically, Cyan at 500 mA (with ~75% maximum flux) and Red-Orange at 700 mA (with ~55% maximum flux), unless otherwise stated. As illustrated in FIG. 2, to smooth the LED element pattern from the excitation light, holographic diffusers (15° angle, from Edmunds Scientific) were placed in front of the LEDs. Light was focused onto the sample imaging area by pairs of 25 mm focal length lenses.

Throughout this investigation, it was necessary to use software algorithms to process and analyze the images to identify beads, cells or other particles and to parameterize them in terms of fluorescence intensity and particle size. Image processing was kept to a relative minimum in order to maintain the integrity of the original raw data, and only consisted of scaling the image to compensate for variation in illumination intensity over the image. Specifically, this consisted of an algorithm which scaled each pixel using the local background compared to the average whole-image background. The size of the local background was modified as appropriate to take into account the expected size range of the particles of interest and the distance represented per pixel (after magnification of the image). For example, in the most common cases in this investigation, of beads with diameters from 3 to 8 um and for cells of diameters from 7 to 15 um, with each pixel representing 4 um of the sample, a window of 60 um (15 pixels across) was found to work quite well in this exemplary system, while not consuming excessive CPU time for processing. After images were compensated for illumination variation, another algorithm searched for particles of interest by identifying local intensity maxima that satisfied statistical rules designed to avoid false positives from random noise, foreign particles (dust, etc.) and structural patterns of the sample chamber (e.g. hemacytometer scribe lines). Primarily, the algorithm looks for a local maximum (bright pixel) that is at least 3 standard deviations above background noise, surrounded by a ring of pixels that are all at least 1.5 standard deviations above background noise, and has subsequent rings of decreasing intensity (allowing for statistical noise variation). Additional checks for culling duplicate particle identifications and checking for reasonable standard deviation values are included. When a particle is identified, another algorithm finds the best-fit simple (circular, not elliptical) Gaussian curve to the particle's intensity profile, using a steepest-descent fitting algorithm on a form of the Gaussian expression optimized for this fitting algorithm. The standard parameters of height, radius, offset and X-Y location are reported, along with fitting statistics (sum of squared residuals and chi-squared) are recorded for each identified particle. Particles are then categorized (or "gated") based on their radius, height and integrated intensity (volume under the Gaussian curve), to separate them into different cytometric populations.

Sensitivity was demonstrated using various specifically prepared beads with low quantities of bound phycoerythrin (PE) molecules per bead. These particles were prepared by incubating BD α-Mouse-Igκ Compensation Beads (Becton Dickinson p/n 552843) incubated with mixtures of antibody specific for CD3 antigen labeled with PE (CD3-PE) and antibody specific for CD3 antigen labeled with biotine (CD3-biotin) in ratios that generated stable beads with very low levels of PE molecules bound per bead. Beads were imaged with the DragonFly2 CCD camera (Point Grey Research, Vancouver, BC) at various exposure durations and internal gain settings. The number of PE molecules per particle for the resulting beads were determined by scaling against PE Quantibrite beads (Becton Dickinson p/n 30495). In this study, the dimmest bead preparation (shown in FIG. 6A) yielded 825 PE molecules per particle, and was detectable from background noise at high gain (24 dB) and intermediate exposure duration (1 s). The 825 PE-molecule bead was the dimmest particle tested and represents a more than adequate level of sensitivity to satisfy any DNA-based cell counting assay (hundreds of thousands of fluorophores per cell), most relevant cell surface markers such as CD3 and CD4 antigens on T-cells (staining at ~150,000 and ~50,000 PE molecules per cell respectively), and many other applications including parasite detection and clinical bead-based assays, e.g. the cytometric bead array disclosed in Morgan et al, Clinical Immunol., 110: 252-266 (2004), which is incorporated herein by reference.

The dynamic range for electronic detectors (including this one) is primarily set by the dynamic range of the A-D converter, and then reduced by signal noise. The 12-bit A-D converter of the Dragonfly2 camera sets a theoretical maximum dynamic range to 1-4096 within a single image. Noise characteristics were investigated for the Dragonfly2 camera, with the two main contributors being read noise and dark current. These were measured by analyzing images taken with gains from 0 to 24 dB and exposure times ranging from 0 to 10 seconds. Fitting the calculated intensity of noise in the images yielded read noise and dark current values for each gain setting. Noise increased linearly with gain and, for a practical range of measurement conditions, consumed from 1.62 bits for 0.1 s exposure at 0 dB gain, to 6.24 bits at 10 s exposure at 24 dB gain. This reduces the dynamic range of a single image to 1-1334 for the best case or 1-54 for the worst case. It is noted that for this system, wherein the sample remains stationary in front of the camera, the effective dynamic range of the instrument can be considerably enhanced by taking multiple images while changing the CCD gain setting and exposure durations on the fly. Since intensity is directly proportional to exposure duration and CCD amplification, under practical conditions this increases the available dynamic range by two to three orders of magnitude.

Figure 9:
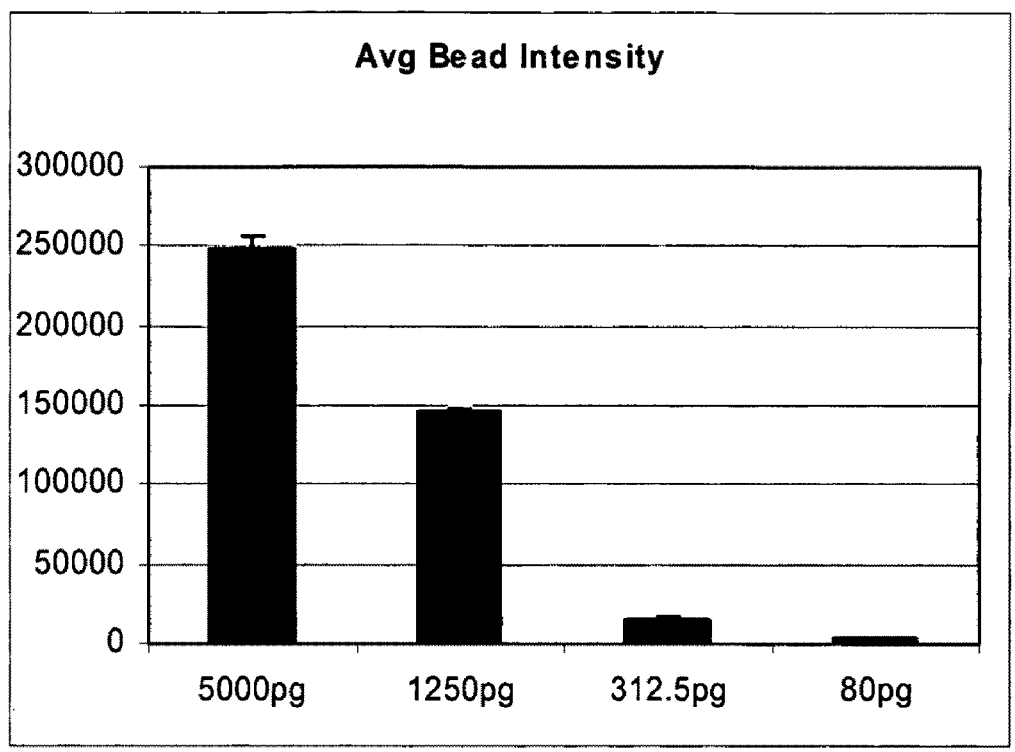
FIG. 9 shows data from a bead-based assay for interleukin-2 concentration.

PE Quantibrite beads, which span ~100-fold intensity change, were used to test this. PE Quantibrite beads consist of a mixture of four populations of beads, each with a specific average number of PE molecules per bead. In this way, detectors can be calibrated to absolute intensity values in terms of PE molecules. Thus, the brightest population contains (on average) 66408 PE molecules per bead, the next population contains 31779 PE molecules per bead, followed by 8612 and 863 PE molecules per bead. PE Quantibrite beads were imaged in a series of increasing exposure durations of 0.1 to 20 seconds and at a span of gain settings (1-15× amplification). As duration and gain was increased, the dynamic range window moved to detect each bead in turn, at increasing intensity levels, until all beads were measured (FIG. 9). In this method, the slope of the best fit lines is proportional to the number of PE molecules per bead and gives a more precise value than using only single images.

The first application investigated on the device was the absolute counting of cultured cells in a volumetric chamber. A live/dead assay was designed in accordance with the two-color excitation and common emission range aspects of the instrument, with the impermeant Propidium Iodide (PI) dye staining dead cells and the permeant SYTO-17 dye staining all cells. PI was excited with the 505 nm (Cyan) LED behind a 510/50 bandpass filter and SYTO-17 was excited with the 617 nm (Red-Orange) LED behind a 610/30 bandpass filter. The emission filter used was a 720/150 bandpass filter, which encompasses roughly one third of the PI emission spectrum and one half of the SYTO-17 emission spectrum (see FIG. 4A, where the following are illustrated: PI adsorption spectrum (400), PI emission spectrum (402), SYTO-17 absorption spectrum (404), SYTO-17 emission spectrum (406), first excitation wavelength range (408), second excitation wavelength range (410), and wavelength range (412) over which optical signals are collected).

Figure 6A:
FIG. 6A is an image of commercially available phycoerythrin-labeled beads disposed on a slide.

Three cell lines (A549, HeLa and U20S) as well as DNA QC particles (Becton Dickinson p/n 349523, including chick erythrocyte nuclei and calf thymus nuclei) were used in the investigation. Since DNA staining is extremely bright relative to cell surface markers or PE Quantibrite beads, the instrument sensitivity was reduced by either decreasing exposure time, gain or excitation LED current (all of which yielded satisfactory results). Image quality and fidelity was excellent for both PI and SYTO-17 staining (FIG. 6A). SYTO-17 can pass through live cell membranes while PI can only pass through membranes which have lost some structural integrity. As the membrane permeability of dying cells increases, PI staining of the nucleus increases. Thus, the balance of PI staining versus SYTO-17 staining in these cells can range from roughly 1:1 to PI intensities several fold higher as PI displaces SYTO-17 from the DNA.

Figure 6B:
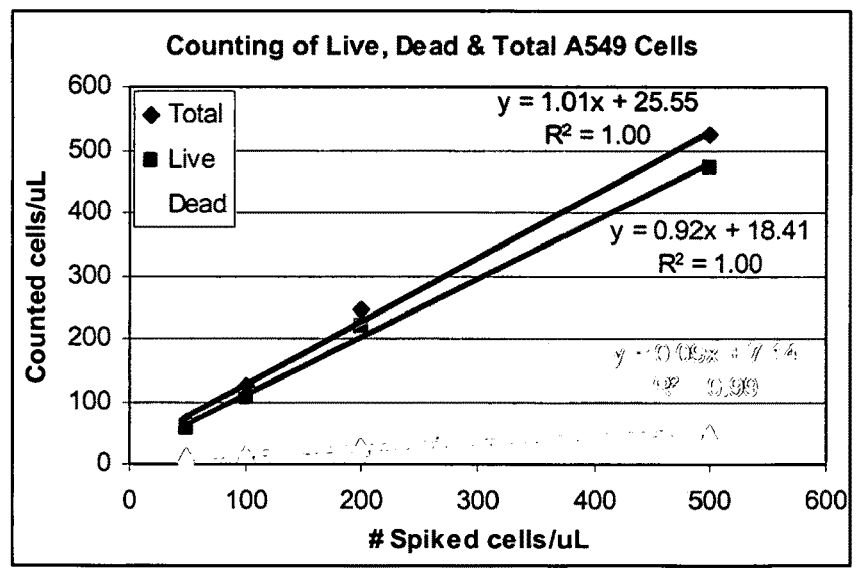
FIG. 6B shows data demonstrating the linear relationship between labeled bead concentration and bead counts.
Figure 7A:
FIG. 7A is an image of cells from whole blood dually labeled with APC-labeled anti-CD3 antibody and PECy5-labeled anti-CD4 antibody.
Figure 7B:
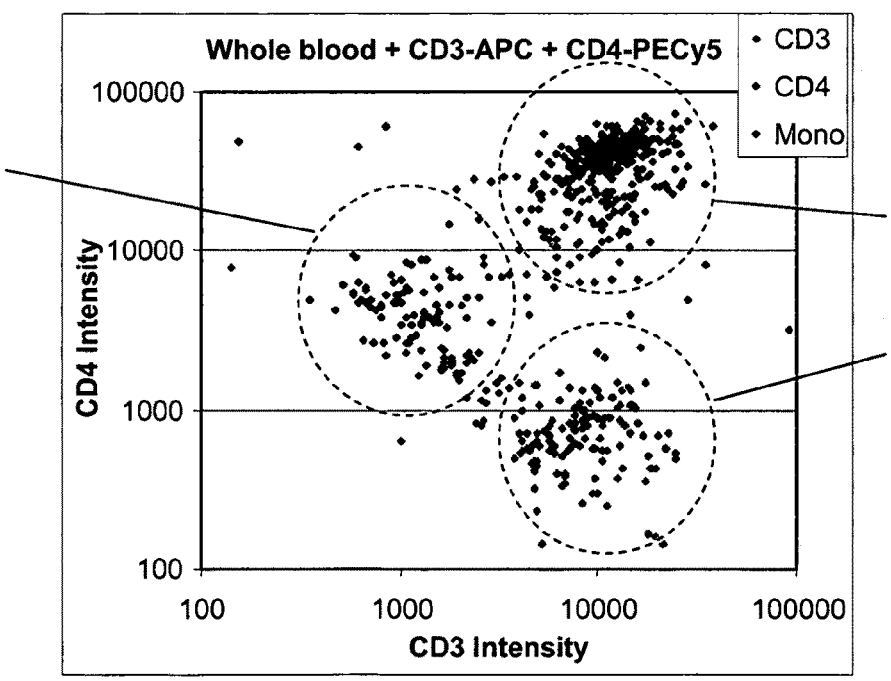
FIG. 7B shows data from FIG. 5A in a two-dimensional plot of APC signal intensity versus PE signal intensity, which shows distinct clusters of three cell types, monocytes, $CD4^+$ T cells, and $CD4^-$ T cells.
Figure 8A:
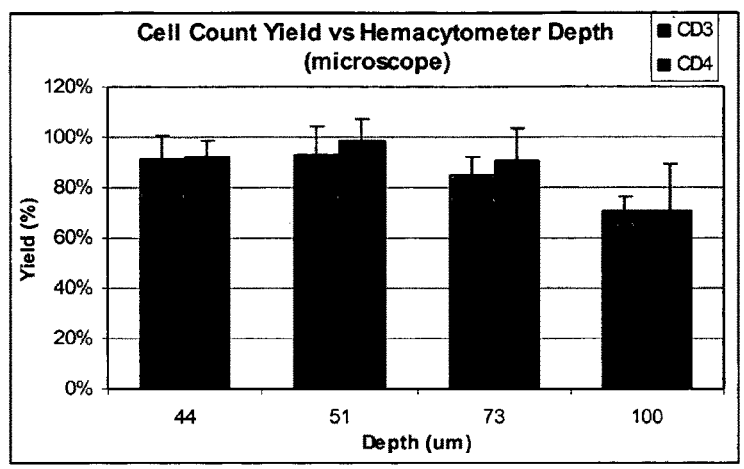
FIGS. 8A-8B show data comparing whole blood cell counts from the apparatus of Example 1 to counts obtained using a flow cytometer, both for different sample cuvette depths (FIG. 6A) and for different labels with a 50 μm (depth) sample cuvette (FIG. 6B).
Figure 8B:
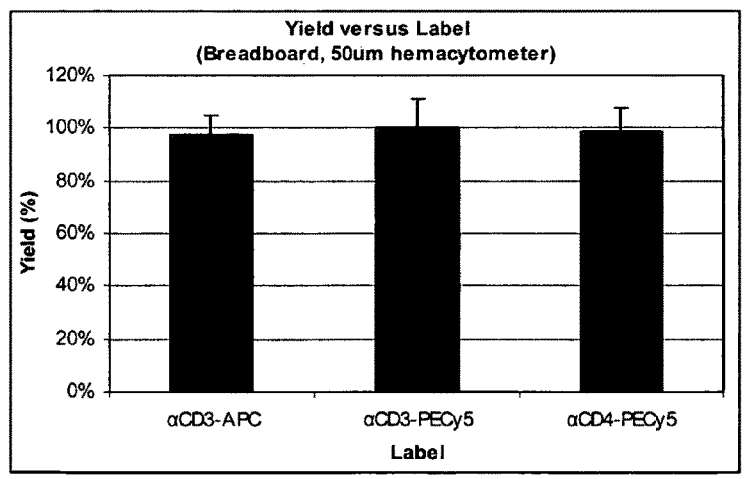

Live and dead cells were differentiated in the resulting image to separately determine live and dead cell counts, as well as total cell counts. In one study, A549 cells, recently trypsinized and detached from a culture flask, were spiked into DMEM cell medium at concentrations ranging from 50 to 500 cells/uL. Each sample was incubated with 10 uM SYTO-17+10 uM PI for 10 minutes and then aliquots from each sample were transferred into a hemacytometer chamber. The sample was imaged in the hemacytometer chamber as described above, and the images were analyzed for live, dead and total cell counts. The linearity results were excellent (see FIG. 6B), with all three counts having $R^2$ values of 0.99 or better. No optimization of the image analysis algorithms or gating processes were conducted, and a background count of ~25 cells/uL from false positives was apparent, although this can be resolved by improvements in the analysis and gating algorithms.

The above system was used to detect and count CD4+ cells in blood samples. With lysed blood samples, results compare very favorably with flow cytometry for enumerating CD3-, CD4- and CD45-positive cells. Both CD3 and CD4 cell surface markers have been used to identify cells in whole blood, by adding fluorescently labeled anti-CD3 and anti-CD4 antibodies respectively with excellent image quality, as illustrated by the data shown in FIGS. 7A-7B and 8A-8B.

The performance of the above system was further tested by counting and quantifying optical signals from conventional bead-based immunoassays. Beads from a BD Bioscience (San Jose, Calif.) cytometric bead assay (CBA) for measuring interleukin-2 (IL-2) were combined with several concentrations of IL-2 and stained with a labeled anti-IL-2 antibody using the manufacturer's protocol, e.g. Morgan et al, Clinical Immunology, 110: 252-266 (2004). Instead of analyzing signals from the bead with a flow cytometer, the labeled beads were imaged in the above system, after which they were counted and classified according to signal intensity. Results are illustrated in FIG. 9.

DEFINITIONS

Generally, terms used herein not otherwise specifically defined have meanings corresponding to their conventional usage in the fields related to the invention, including analytical chemistry, biochemistry, molecular biology, cell biology, microscopy, image analysis, and the like, such as represented in the following treatises: Alberts et al, Molecular Biology of the Cell, Fourth Edition (Garland, 2002); Nelson and Cox, Lehninger Principles of Biochemistry, Fourth Edition (W.H. Freeman, 2004); Murphy, Fundamentals of Light Microscopy and Electronic Imaging (Wiley-Liss, 2001); Shapiro, Practical Flow Cytometry, Fourth Edition (Wiley-Liss, 2003); and the like.

"Analyte" means a substance, compound, or component in a sample whose presence or absence is to be detected or whose quantity is to be measured. Analytes include but are not limited to peptides, proteins, polynucleotides, polypeptides, oligonucleotides, organic molecules, haptens, epitopes, parts of biological cells, posttranslational modifications of proteins, receptors, complex sugars, vitamins, hormones, and the like. There may be more than one analyte associated with a single molecular entity, e.g. different phosphorylation sites on the same protein.

"Antibody" or "immunoglobulin" means a protein, either natural or synthetically produced by recombinant or chemical means, that is capable of specifically binding to a particular antigen or antigenic determinant. Antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. The constant domains are not involved directly in binding an antibody to an antigen. Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG, $IgG_2$, $IgG_3$, $IgG_4$, $IgA_1$, and $IgA_2$. "Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (I) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture, uncontaminated by other immunoglobulins. Guidance in the production and selection of antibodies for use in immunoassays can be found in readily available texts and manuals, e.g. Harlow and Lane, Antibodies: A Laboratory Manual (Cold Spring Harbor Laboratory Press, New York, 1988); Howard and Bethell, Basic Methods in Antibody Production and Characterization (CRC Press, 2001); Wild, editor, The Immunoassay Handbook (Stockton Press, New York, 1994), and the like.

"Antigenic determinant," or "epitope" means a site on the surface of a molecule, usually a protein, to which a single antibody molecule binds; generally a protein has several or many different antigenic determinants and reacts with antibodies of many different specificities. A preferred antigenic determinant is a phosphorylation site of a protein.

"Binding compound" means a compound that is capable of specifically binding to a particular target molecule. Examples of binding compounds include antibodies, lectins, nucleic acids, aptamers, and the like, e.g. Sharon and Lis, Lectins, $2^{nd}$ Edition (Springer, 2006); Klussmann, The Aptamer Handbook: Functional Oligonucleotides and Their Applications (John Wiley & Sons, New York, 2006).

"Complex" as used herein means an assemblage or aggregate of molecules in direct or indirect contact with one another. In one aspect, "contact," or more particularly, "direct contact" in reference to a complex of molecules, or in reference to specificity or specific binding, means two or more molecules are close enough so that attractive noncovalent interactions, such as Van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. As used herein, "complex" usually refers to a stable aggregate of two or more proteins. In one aspect, a "complex" refers to a stable aggregate of two proteins, such as an antibody specifically bound to an antigenic determinant of a target protein.

"Dried reagents" mean assay reagents, such as buffers, salts, active compounds, such as enzymes, co-factors, and the like, or binding compounds, such as antibodies, aptamers, or the like, that are provided in a dehydrated formulation for the purpose of improved shelf-life, ease of transport and handling, improved storage, and the like. The nature, composition, and method of producing dried reagents vary widely and the formulation and production of such materials is well-known to those of ordinary skill in the art as evidenced by the following references that are incorporated by reference: Franks et al, U.S. Pat. No. 5,098,893; Cole, U.S. Pat. No. 5,102,788; Shen et al, U.S. Pat. No. 5,556,771; Treml et al, U.S. Pat. No. 5,763,157; De Rosier et al, U.S. Pat. No. 6,294,365; Buhl et al, U.S. Pat. No. 5,413,732; McMillan, U.S. patent publication 2006/0068398; McMillan et al, U.S. patent publication 2006/0068399; Schwegman et al (2005), Pharm. Dev. Technol., 10: 151-173; Nail et al (2002), Pharm. Biotechnol., 14: 281-360; and the like. Dried reagents include, but are not limited to, solid and/or semi-solid particulates, powders, tablets, crystals, capsules and the like, that are manufactured in a variety of ways. In one aspect, dried reagents are lyophilized particulates. Lyophilized particulates may have uniform compositions, wherein each particulate has the same composition, or they may have different compositions, such that two or more different kinds of lyophilized particulates having different compositions are mixed together. Lyophilized particulates can contain reagents for all or part of a wide variety of assays and biochemical reactions, including immunoassays, enzyme-based assays, enzyme substrate assays, DNA sequencing reactions, and the like. In one aspect, a lyophilized particulate of the invention comprises an excipient and at least one reagent of an assay. Lyophilized particulates may be manufactured in predetermined sizes and shapes, which may be determined by the type of assay being conducted, desired reaction volume, desired speed of dissolution, and the like. Dried reagents may include excipients, which are usually inert substances added to a material in order to confer a suitable consistency or form to the material. A large number of excipients are known to those of skill in the art and can comprise a number of different chemical structures. Examples of excipients, which may be used in the present invention, include carbohydrates, such as sucrose, glucose, trehalose, melezitose, dextran, and mannitol; proteins such as BSA, gelatin, and collagen; and polymers such as PEG and polyvinyl pyrrolidone (PVP). The total amount of excipient in the lyophilized particulate may comprise either single or multiple compounds. In some embodiments, the type of excipient is a factor in controlling the amount of hygroscopy of a dried reagent. Lowering hygroscopy can enhance the dried reagent's integrity and cryoprotectant abilities. However, removing all water from such a composition would have deleterious effects on those reaction components, proteins for example, that require certain amounts of bound water in order to maintain proper conformations.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the position and fluorescence intensity of a signal being generated at each hybridization site of the microarray; thus, such a readout may be registered or stored in various ways, for example, as an image of the microarray, as a table of numbers, or the like.

"Sample" means a quantity of material from a biological, environmental, medical, or patient source in which detection or measurement of target cells, particles, beads, and/or analytes is sought. The term "sample" encompasses biological samples, e.g. a quantity of blood, a microbiological culture, or the like; environmental samples, e.g. a soil or water sample; medical samples or specimens, e.g. a quantity of blood or tissue; or the like. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. The terms "sample" and "specimen" are used interchangeably.

"Specific" or "specificity" in reference to the binding of one molecule to another molecule means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least thirty percent. Generally, molecules involved in a specific binding event have areas on their surfaces, and/or in the case of proteins in cavities, giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

What is claimed is:

1. A disposable blood collection cuvette for optical analysis of non-red blood cells, the cuvette comprising:
   a mixing chamber having an inlet for accepting a sample of whole blood, the mixing chamber further comprising a dried reagent capable of dissolving on contact with the whole blood sample and containing a probe composition that comprises a plurality of analyte-specific probes, each capable of binding specifically to a different cellular analyte of a non-red blood cell, wherein each probe is characterized by (a) a binding compound specific for a cellular analyte under binding conditions, and (b) attached to the binding compound an optical label, wherein the optical label of each different probe has a different excitation band and the optical labels of all probes emit optical signals within the same wavelength range; and
   a sample chamber fluidly connected to the mixing chamber so that a sample in the mixing chamber is transferred to the sample chamber by capillary action, the sample chamber having an optically transmissive wall and a dimension perpendicular thereto, wherein the dimension of the sample chamber perpendicular to said optically transmissive wall is in the range from 10 to 120 μm.

2. The cuvette of claim 1 wherein said dimension substantially precludes the formation of a light-obstructing layer of enucleate red blood cells between a cell of interest and said optically transmissive wall.

3. The disposable blood collection cuvette of claim 1, wherein the dimension of the sample chamber perpendicular to said optically transmissive wall is in the range from 40 to 120 μm.

4. The disposable blood collection cuvette of claim 1, wherein the dimension of the sample chamber perpendicular to said optically transmissive wall is in the range from 50 to 100 μm.

5. The disposable blood collection cuvette of claim 1, wherein the dimension of the sample chamber perpendicular to said optically transmissive wall is in the range from 10 to 100 μm.

6. The disposable blood collection cuvette of claim 1, wherein the dimension of the sample chamber perpendicular to said optically transmissive wall is in the range from 10 to 50 μm.

7. The disposable blood collection cuvette of claim 1, wherein the dimension of the sample chamber perpendicular to said optically transmissive wall is in the range from 20 to 50 μm.

* * * * *